(12) United States Patent
Marchiarullo et al.

(10) Patent No.: US 9,833,182 B2
(45) Date of Patent: Dec. 5, 2017

(54) BIOLOGICAL FLUID SEPARATION DEVICE AND BIOLOGICAL FLUID SEPARATION AND TESTING SYSTEM

(71) Applicant: Becton, Dickinson and Company, Franklin Lakes, NJ (US)

(72) Inventors: Daniel J. Marchiarullo, Morris Plains, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/251,699

(22) Filed: Apr. 14, 2014

(65) Prior Publication Data

US 2014/0308179 A1    Oct. 16, 2014

Related U.S. Application Data

(60) Provisional application No. 61/811,918, filed on Apr. 15, 2013.

(51) Int. Cl.
*A61B 5/15* (2006.01)
*G01N 33/49* (2006.01)
(Continued)

(52) U.S. Cl.
CPC ...... *A61B 5/150213* (2013.01); *A61B 5/1411* (2013.01); *A61B 5/151* (2013.01);
(Continued)

(58) Field of Classification Search
CPC ........ A61B 5/150213; A61B 5/150305; G01N 33/491; G01N 1/4005
See application file for complete search history.

(56) References Cited

U.S. PATENT DOCUMENTS 3,322,114 A    5/1967  Portnoy et al.
3,640,393 A    2/1972  Hurtig
(Continued)

FOREIGN PATENT DOCUMENTS

CN    1382966 A    12/2002
CN    101102847 A    1/2008
(Continued)

OTHER PUBLICATIONS

Membrane Separation Technology for Research and Quality Control, Sartorius AG, Separation Technology, Laboratory Filtration; Mar. 1, 1997.

*Primary Examiner* — Sam P Siefke
(74) *Attorney, Agent, or Firm* — The Webb Law Firm

(57) ABSTRACT

A biological fluid separation device that is adapted to receive a multi-component blood sample is disclosed. After collecting the blood sample, the biological fluid separation device is able to separate a plasma portion from a cellular portion. After separation, the biological fluid separation device is able to transfer the plasma portion of the blood sample to a point-of-care testing device. The biological fluid separation device of the present disclosure also provides a closed separation and transfer system that reduces the exposure of a blood sample and provides fast mixing of a blood sample with a sample stabilizer. The biological fluid separation device is engageable with a blood testing device for closed transfer of a portion of the plasma portion from the biological fluid separation device to the blood testing device. The blood testing device is adapted to receive the plasma portion to analyze the blood sample and obtain test results.

14 Claims, 10 Drawing Sheets

(51) Int. Cl.
*A61M 1/34* (2006.01)
*G01N 1/28* (2006.01)
*G01N 1/40* (2006.01)
*G01N 1/34* (2006.01)
*B01L 3/00* (2006.01)
*B04B 7/08* (2006.01)
*A61B 5/151* (2006.01)
*A61B 5/157* (2006.01)

(52) U.S. Cl.
CPC ........ *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150748* (2013.01); *A61B 5/150755* (2013.01); *A61B 5/150778* (2013.01); *A61M 1/34* (2013.01); *B01L 3/502* (2013.01); *B01L 3/5021* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150442* (2013.01); *A61B 5/150969* (2013.01); *B01L 2200/0631* (2013.01); *B01L 2200/10* (2013.01); *B01L 2300/0681* (2013.01); *B01L 2400/0478* (2013.01); *G01N 2001/4016* (2013.01); *G01N 2001/4088* (2013.01)

(56) References Cited

U.S. PATENT DOCUMENTS

| | | | |
|---|---|---|---|
| 4,511,349 A | 4/1985 | Nielsen et al. | |
| 4,627,445 A | 12/1986 | Garcia et al. | |
| 5,055,203 A | 10/1991 | Columbus | |
| 5,163,442 A | 11/1992 | Ono | |
| 5,219,999 A | 6/1993 | Suzuki et al. | |
| 5,422,018 A | 6/1995 | Saunders et al. | |
| 5,636,640 A | 6/1997 | Staehlin | |
| 5,726,026 A | 3/1998 | Wilding et al. | |
| 5,839,715 A | 11/1998 | Leinsing | |
| 5,922,591 A | 7/1999 | Anderson et al. | |
| 6,074,183 A | 6/2000 | Allen et al. | |
| 6,264,619 B1 | 7/2001 | Ferguson | |
| 6,506,167 B1 | 1/2003 | Ishimito et al. | |
| 6,869,405 B2 | 3/2005 | Marsden | |
| 7,378,259 B2 * | 5/2008 | Bahatt | B01L 3/5027 435/6.1 |
| 8,158,410 B2 | 4/2012 | Tang et al. | |
| 2002/0009015 A1 | 1/2002 | Laugharn, Jr. et al. | |
| 2002/0143298 A1 | 10/2002 | Marsden | |
| 2003/0134416 A1 | 7/2003 | Yamanishi et al. | |
| 2004/0142463 A1 | 7/2004 | Walker et al. | |
| 2004/0143226 A1 | 7/2004 | Marsden | |
| 2004/0230216 A1 | 11/2004 | Levaughn et al. | |
| 2005/0069459 A1 | 3/2005 | Ahn et al. | |
| 2005/0214927 A1 | 9/2005 | Haley | |
| 2006/0029923 A1 | 2/2006 | Togawa et al. | |
| 2006/0240964 A1 | 10/2006 | Lolachi et al. | |
| 2007/0031283 A1 | 2/2007 | Davis et al. | |
| 2007/0160503 A1 | 7/2007 | Sethu et al. | |
| 2008/0135502 A1 | 6/2008 | Pyo et al. | |
| 2008/0240990 A1 | 10/2008 | Flaherty | |
| 2009/0004060 A1 | 1/2009 | Omuro et al. | |
| 2009/0136982 A1 | 5/2009 | Tang et al. | |
| 2009/0181411 A1 | 7/2009 | Battrell et al. | |
| 2009/0204026 A1 | 8/2009 | Crawford et al. | |
| 2010/0089815 A1 | 4/2010 | Zhang et al. | |
| 2010/0093551 A1 | 4/2010 | Montagu | |
| 2010/0198108 A1 | 8/2010 | Alden | |
| 2010/0241031 A1 | 9/2010 | Lai | |
| 2011/0009717 A1 | 1/2011 | Davis et al. | |
| 2011/0124130 A1 | 5/2011 | Wagner et al. | |
| 2011/0124984 A1 | 5/2011 | Rostaing | |
| 2012/0152858 A1 | 6/2012 | Yang | |
| 2012/0275955 A1 | 11/2012 | Haghgooie et al. | |
| 2012/0277696 A1 | 11/2012 | Gonzalez-Zugasti et al. | |
| 2012/0277697 A1 | 11/2012 | Haghgooie et al. | |
| 2013/0026085 A1 | 1/2013 | Samsoondar | |
| 2013/0052675 A1 | 2/2013 | Karlsson et al. | |
| 2013/0082012 A1 | 4/2013 | Lean et al. | |
| 2013/0086980 A1 | 4/2013 | Gadini et al. | |
| 2013/0175213 A1 | 7/2013 | Dorrer et al. | |
| 2013/0209331 A1 | 8/2013 | Rodenfels et al. | |

FOREIGN PATENT DOCUMENTS

| | | |
|---|---|---|
| CN | 101332320 A | 12/2008 |
| CN | 102764133 A | 11/2012 |
| DE | 202008010918 U1 | 1/2009 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 2/2012 |
| FR | 2929135 A1 | 10/2009 |
| FR | 2977808 A1 | 1/2013 |
| JP | 2004361419 A | 12/2004 |
| JP | 2012532683 A | 12/2012 |
| WO | 9309710 A1 | 5/1993 |
| WO | 2005018710 A2 | 3/2005 |
| WO | 2006047831 A1 | 5/2006 |
| WO | 2007002579 A2 | 1/2007 |
| WO | 2009123592 A1 | 10/2009 |
| WO | 2011040874 A1 | 4/2011 |
| WO | 2012121686 A1 | 9/2012 |

* cited by examiner

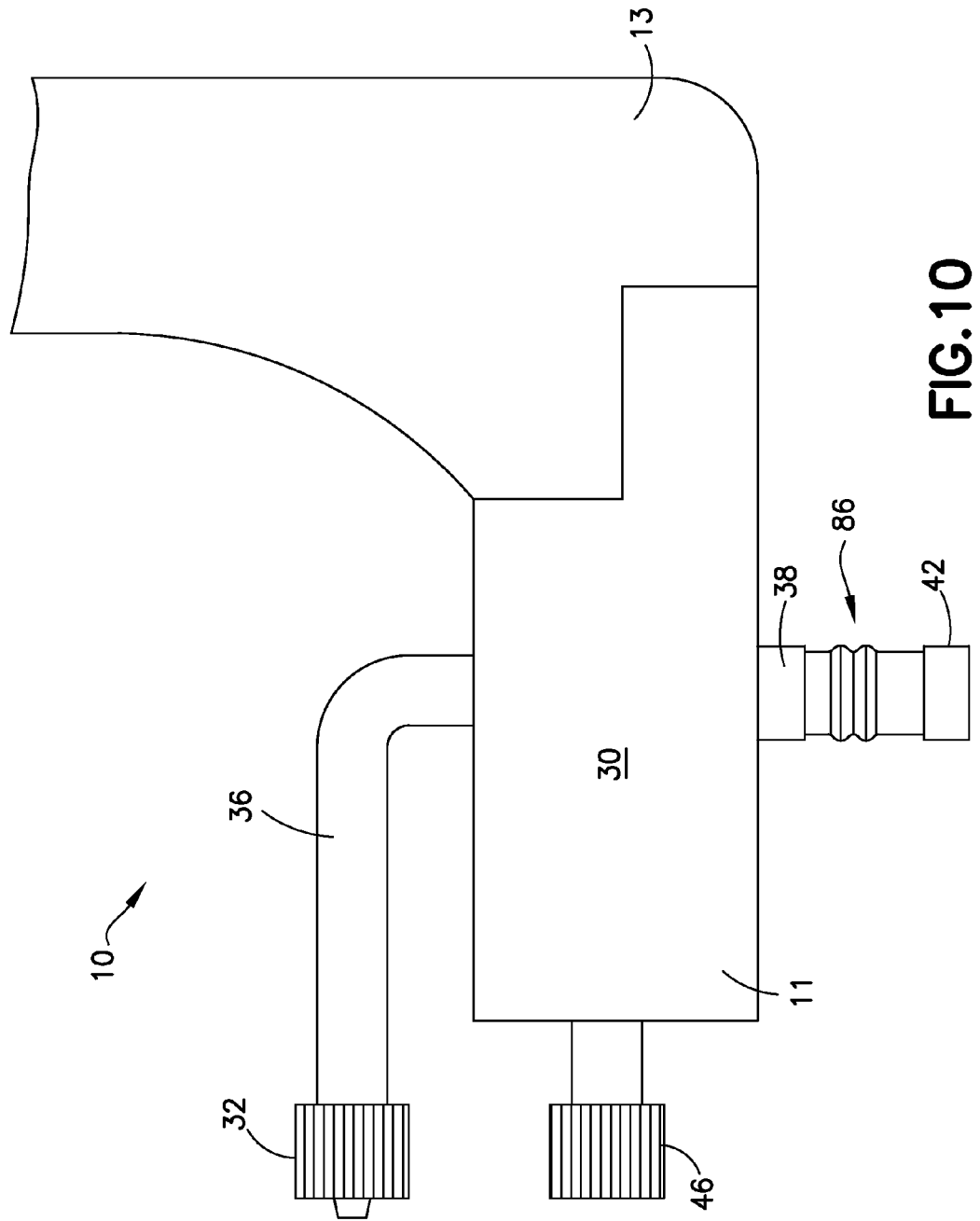

BIOLOGICAL FLUID SEPARATION DEVICE AND BIOLOGICAL FLUID SEPARATION AND TESTING SYSTEM

CROSS REFERENCE TO RELATED APPLICATIONS

The present application claims priority to U.S. Provisional Application No. 61/811,918, filed Apr. 15, 2013, entitled "Medical Device for Collection of a Biological Sample", the entire disclosure of which is hereby incorporated by reference in its entirety.

BACKGROUND OF THE INVENTION

1. Field of the Disclosure

The present disclosure relates generally to devices, assemblies, and systems adapted for use with vascular access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid separation device, such as a blood separation device, that is adapted to receive a multi-component blood sample, for example, having a cellular portion and a plasma portion. After collecting the blood sample, the blood separation device is able to separate the plasma portion from the cellular portion. After separation, the blood separation device is able to transfer the plasma portion of the blood sample to a point-of-care testing device. The blood separation device of the present disclosure also provides a closed separation system that reduces the exposure of a blood sample and provides fast mixing of a blood sample with a sample stabilizer, which could be an anticoagulant, or a substance designed to preserve a specific element within the blood such as, for example, RNA, protein analyte, or other element. The blood separation device is engageable with a blood testing device for closed transfer of a portion of the plasma portion from the blood separation device to the blood testing device. The blood testing device is adapted to receive the plasma portion to analyze the blood sample and obtain test results.

Some of the advantages of the blood separation device and the biological fluid separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to a point-of-care testing device. The blood separation device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the blood separation device of the present disclosure minimizes process time by processing the blood within the blood separation device and without external machinery. Further, for tests which only require small amounts of blood, it eliminates the waste associated with blood collection and plasma separation with an evacuated tube.

In accordance with an embodiment of the present invention, a biological fluid separation cartridge, such as a blood separation cartridge, includes a housing having an inlet port and a flow channel defined within the housing in fluid communication with the inlet port, a first collection chamber defined within the housing in fluid communication with the flow channel and including a first outlet port, and a second collection chamber defined within the housing in fluid communication with the flow channel and including a second outlet port. The second collection chamber is isolated from the first collection chamber, and the second outlet port is spaced apart from the first outlet port.

In certain configurations, the flow channel has a spiral shape. At least a portion of the flow channel may include a sample stabilizer. In certain arrangements, the cartridge may include an inlet channel in fluid communication with the inlet port and the flow channel, with the inlet channel including a sample stabilizer. The biological fluid separation cartridge may be adapted to receive a multi-component blood sample. The multi-component blood sample may include a cellular portion and a plasma portion.

The cartridge may include a flow channel having a separation element adapted to separate the cellular portion and the plasma portion of the multi-component blood sample. The separation element may include a plurality of posts. In certain configurations, the inlet port may be adapted to receive the multi-component blood sample via connection to a blood collection device. The first collection chamber may be adapted to receive at least a portion of the plasma portion therein, and the second collection chamber may be adapted to receive at least a portion of the cellular portion. In some cases, the cellular portion is prevented from entering the first collection chamber. The first outlet port may be adapted for connection to a point-of-care testing device for closed transfer of a portion of the plasma portion from the first collection chamber to the point-of-care testing device. In other configurations, a portion of the blood separation cartridge is adapted for connection with a drive device. When the drive device is connected to the blood separation cartridge, the drive device causes flow of the plasma portion from the first collection chamber to the point-of-care testing device.

In accordance with another embodiment of the present invention, a biological fluid separation device is adapted to receive a multi-component blood sample. The blood separation device includes a separation cartridge having an inlet port and a flow channel defined within the cartridge in fluid communication with the inlet port. The flow channel contains a separation element adapted to separate the multi-component blood sample into at least a first component and a second component. A first collection chamber defined within the cartridge in fluid communication with the flow channel includes a first outlet port, and a second collection chamber defined within the cartridge in fluid communication with the flow channel includes a second outlet port, with the second collection chamber isolated from the first collection chamber.

In certain configurations, the first component is a cellular portion of the multi-component blood sample and the second component is a plasma portion of the multi-component blood sample. The separation element may include a plurality of posts. In certain embodiments, the flow channel has a spiral shape. The inlet channel may be provided in fluid communication with the inlet port and the flow channel, with the inlet channel including a sample stabilizer. In certain embodiments, the second component is a plasma portion of the multi-component blood sample.

In specific arrangements, the first collection chamber is adapted to receive at least a portion of the second component therein and the second collection chamber is adapted to receive at least a portion of the first component. The first component may be a cellular portion of the multi-component blood sample and the second component may be a plasma portion of the multi-component blood sample. In certain embodiments, the cellular portion is prevented from entering the first collection chamber. Optionally, at least a portion of the flow channel includes a sample stabilizer. The second component may be a plasma portion of the multi-component blood sample.

In certain configurations, the inlet port is adapted to receive the multi-component blood sample via connection to a blood collection device. The first outlet port may be adapted for connection to a point-of-care testing device for closed transfer of a portion of the second component of the multi-component blood sample from the first collection chamber to the point-of-care testing device. A portion of the blood separation device may be adapted for connection with a drive device. When the drive device is connected to the blood separation device, the drive device causes flow of the second component of the multi-component blood sample from the first collection chamber to the point-of-care testing device.

In accordance with yet another embodiment of the present invention, a biological fluid separation and testing system, such as a blood separation and testing system, for a multi-component blood sample includes a blood separation cartridge adapted to receive the multi-component blood sample. The blood separation cartridge includes a housing having an inlet port and a flow channel defined within the housing in fluid communication with the inlet port. The cartridge further includes a first collection chamber defined within the housing in fluid communication with the flow channel and including a first outlet port, and a second collection chamber defined within the housing in fluid communication with the flow channel and including a second outlet port. The second collection chamber is isolated from the first collection chamber, and the second outlet port is spaced apart from the first outlet port. The system further includes a blood testing device having a receiving port adapted to receive the first outlet port of the blood separation cartridge for closed transfer of a portion of a component of the multi-component blood sample from the first collection chamber to the blood testing device.

In certain configurations, the multi-component blood sample includes a first cellular portion component and a second plasma portion component. A portion of the blood separation cartridge may be adapted for connection with a drive device. When the drive device is connected to the blood separation cartridge, the drive device causes flow of the plasma portion from the first collection chamber to the blood testing device. The blood testing device may include a point-of-care testing device.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 10 is a side elevation view of a biological fluid separation device in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
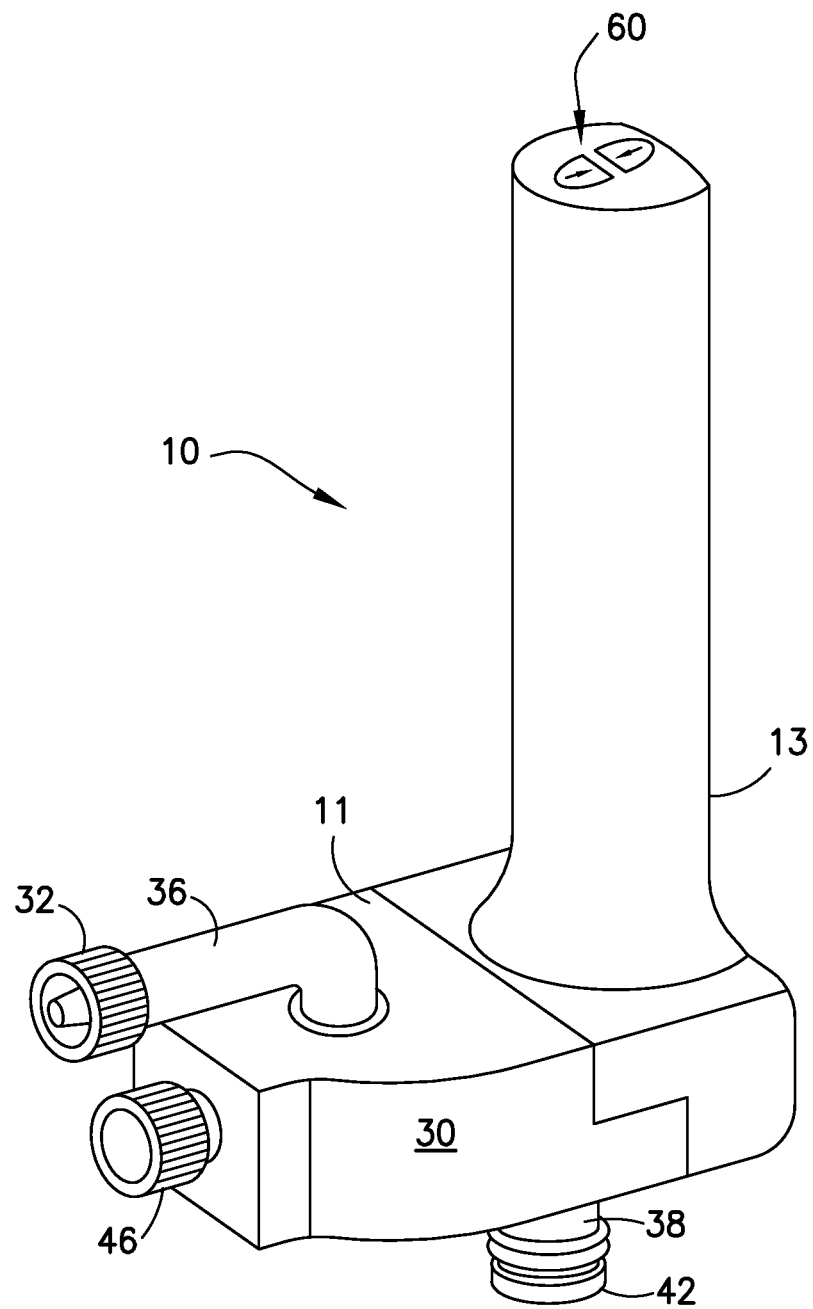
FIG. 1 is a perspective view of a biological fluid separation device in accordance with an embodiment of the present invention.
Figure 2:
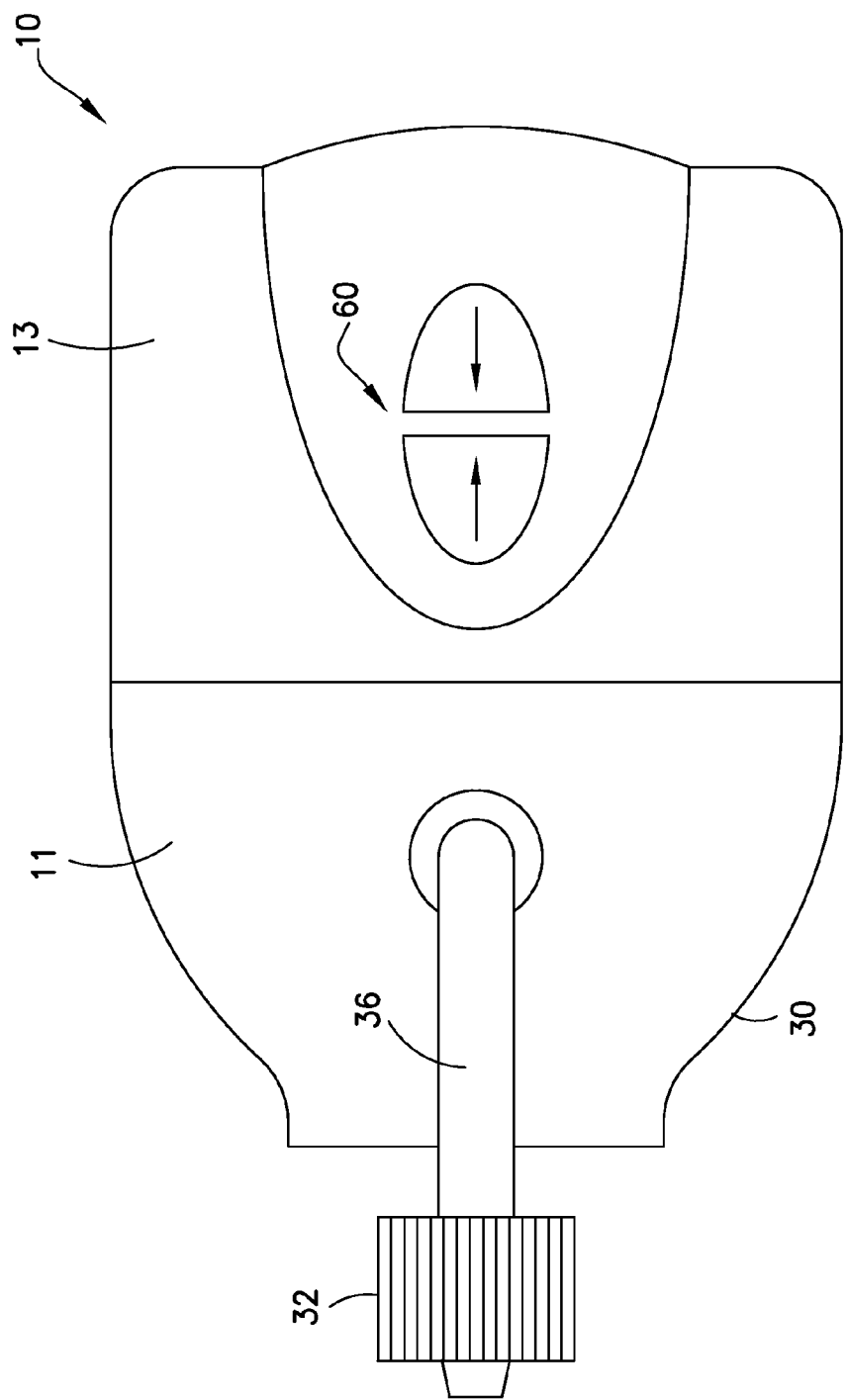
FIG. 2 is a top view of a biological fluid separation device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, or failure of the cartridge leading to a repeat of the sample collection and testing process, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; and 5) separating the sample at the point of collection.

FIGS. 1-11 illustrate an exemplary embodiment of the present disclosure. Referring to FIGS. 1-11, a biological fluid separation device, such as a blood separation device 10, of the present disclosure is adapted to receive a blood sample 12 having a cellular portion 14 and a plasma portion 16. After collecting the blood sample 12, the blood separation device 10 is able to separate the plasma portion 16 from the cellular portion 14. After separation, the blood separation device 10 is able to transfer the plasma portion 16 of the blood sample 12 to a point-of-care testing device. The blood separation device 10 of the present disclosure also provides a closed separation system that reduces the exposure of a blood sample and provides fast mixing of a blood sample with a sample stabilizer.

Figure 6:
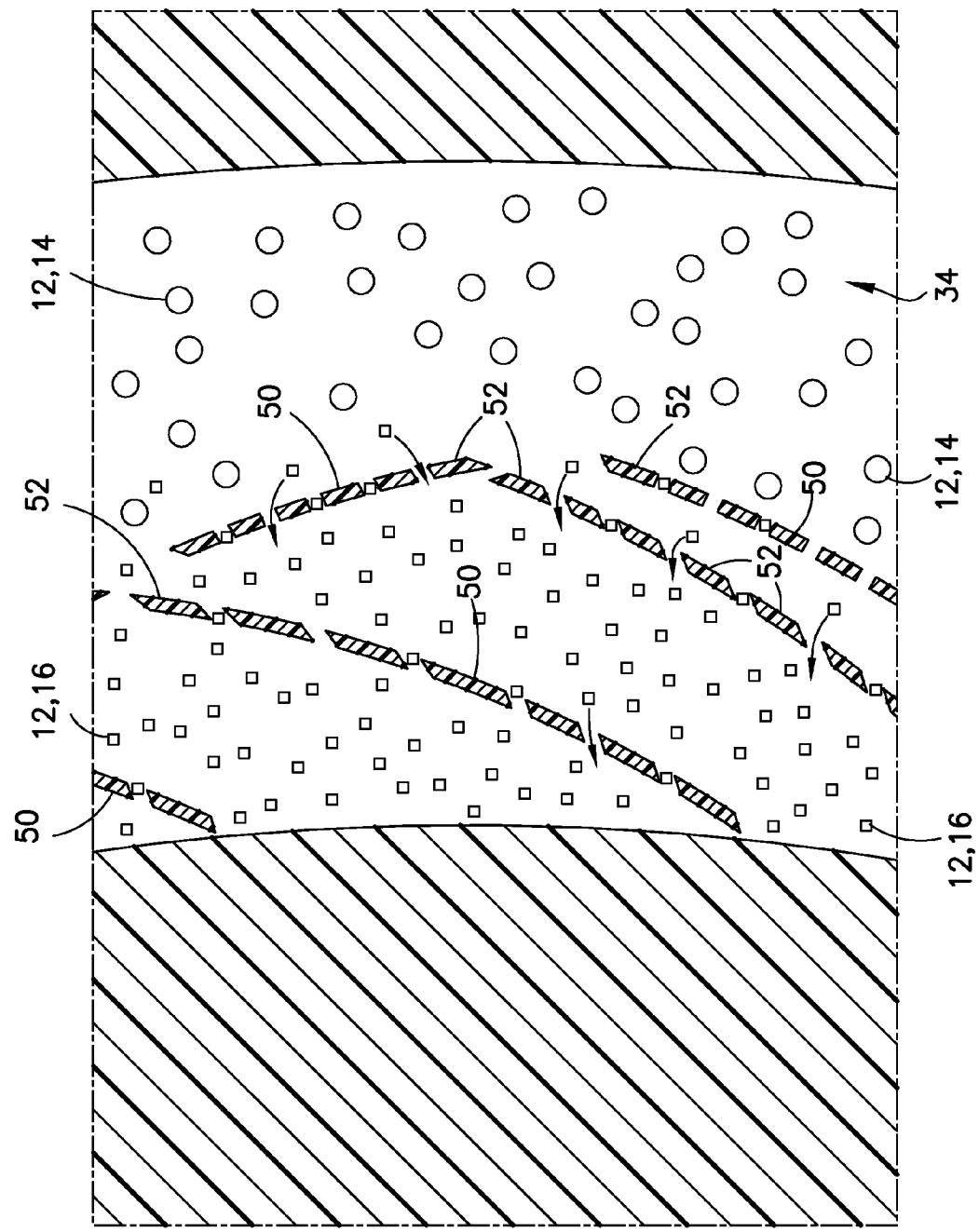
FIG. 6 is a detailed, fragmentary view of a portion of FIG. 5.
Figure 7:
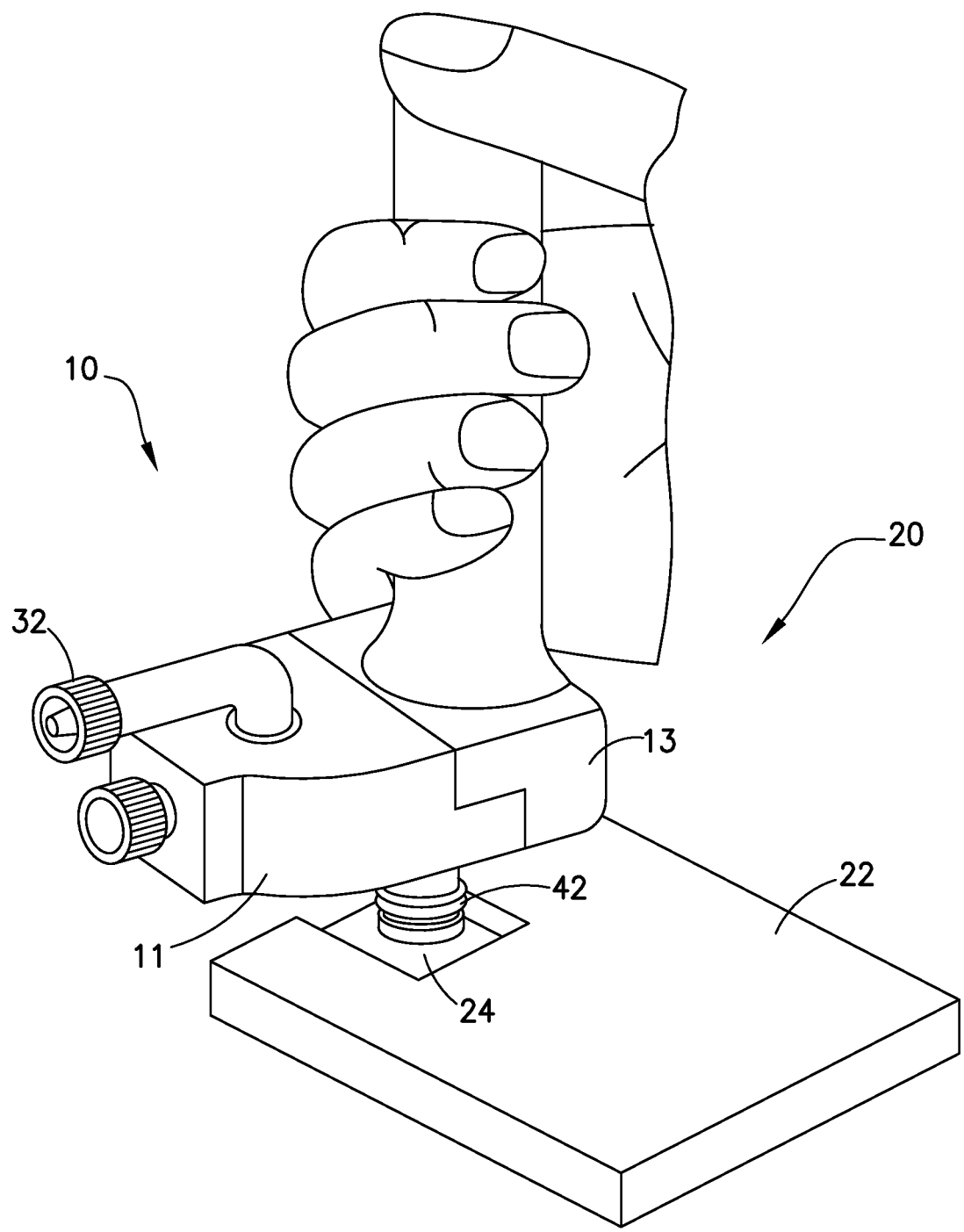
FIG. 7 is a perspective view of a biological fluid separation device and a point-of-care testing device in accordance with an embodiment of the present invention.

FIG. 7 illustrates an exemplary embodiment of the present disclosure. Referring to FIG. 7, a biological fluid separation and testing system, such as a blood separation and testing system 20 of the present disclosure, includes a blood separation device 10 and a blood testing device or point-of-care testing device 22 engageable with the blood separation device 10 for closed transfer of a portion of the plasma portion 16 (FIG. 6) from the blood separation device 10 to the blood testing device 22. The blood testing device 22 is adapted to receive the plasma portion 16 to analyze the blood sample and obtain test results.

Some of the advantages of the blood separation device and the blood separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to a point-of-care testing device. The blood separation device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the blood separation device of the present disclosure minimizes process time by processing the blood within the blood separation device and without external machinery. Further, for tests which only require small amounts of blood, it eliminates the waste associated with blood collection and plasma separation with an evacuated tube.

Referring to FIGS. 1-11, a blood separation device 10 includes a first component or biological fluid separation cartridge, such as a blood separation cartridge 11 and a second component or drive device 13 that is removably connected to the blood separation cartridge 11. The blood separation cartridge 11 is adapted to receive a blood sample 12 having a cellular portion 14 and a plasma portion 16. In one embodiment, a blood separation cartridge 11 is a disposable component and connects with a reusable drive device 13 that is in the shape of a standard pipette which drives the flow of blood through the blood separation cartridge 11 and drives the flow of plasma into a point-of-care testing device 22.

Referring to FIGS. 1-11, the blood separation cartridge 11 generally includes a housing 30, an inlet port 32, a flow channel 34 having an inlet channel 36 and an exit channel 38, a first collection chamber 40 defined within the housing 30 and in fluid communication with the flow channel 34 and including a first outlet port 42, a second collection chamber 44 defined within the housing 30 and in fluid communication with the flow channel 34 and including a second outlet port 46, and a valve or septum 86 disposed at the first outlet port 42. In one embodiment, the second collection chamber 44 is isolated from the first collection chamber 40 and the second outlet port 46 is spaced apart from the first outlet port 42. Referring to FIG. 6, the flow channel 34 includes a separation element 50 that is adapted to separate the cellular portion 14 and the plasma portion 16 of the blood sample 12. In one embodiment, the separation element 50 includes a plurality of posts 52. The inlet channel 36 is in fluid communication with the inlet port 32.

In one embodiment, the blood separation cartridge 11 is connectable with the drive device 13 to allow vacuum or pressure to drive flow of a blood sample within the blood separation cartridge 11. The connection between the blood separation cartridge 11 and the drive device 13 does not allow blood contact with the drive device 13. For example, the use of materials that only let air to pass, or one way valves, ensures that blood does not come in contact with the drive device 13.

In one embodiment, the flow channel 34 has a spiral shape for inertial separation of blood cells, e.g., a cellular portion 14, from a plasma portion 16 as shown in FIG. 6. In one embodiment, the flow channel 34 includes a plurality of posts 52 arranged to enhance plasma separation by filtering and directing the cellular portion 14 to the outside of the flow channel 34, which is the same direction the inertial forces drive the cellular portion 14. The posts 52 can be of any suitable shape, such as rounded, and may have a generally circular cross-section. In another configuration, the posts 52 may have any polygon shape, such as a polygon cross-sectional shape.

At the end of the flow channel 34, e.g., a junction point 48, the flow channel 34 splits into a first collection chamber 40 for collecting the plasma portion 16 and a second collection chamber 44 for collecting the cellular portion 14. The first collection chamber 40 and the second collection chamber 44 includes no posts 52 to take advantage of laminar flow properties in a microfluidic channel. In one embodiment, to increase throughput, multiple spirals can be fabricated that operate in parallel to generate sufficient plasma volume for a downstream application. The first collection chamber 40 includes the first outlet port 42 which interfaces with a point-of-care testing device 22 or storage vessel as discussed in more detail below. The second outlet port 46 provides an outlet for the cellular portion 14 of the blood sample 12. In one embodiment, the junction point 48 contains a mechanism for substantially preventing the cellular portion 14 from entering the first collection chamber 40. For example, the junction point 48 may contain a filter or one-way valve or other mechanism.

In one embodiment, at least a portion of the flow channel 34 is adapted to contain a sample stabilizer to provide passive and fast mixing of a blood sample with the sample stabilizer. The sample stabilizer can be an anticoagulant, or a substance designed to preserve a specific element within the blood such as, for example, RNA, protein analyte, or other element. In other embodiments, the sample stabilizer is provided in other areas of the housing 30 of the blood separation cartridge 11 such as the inlet channel 36. In this manner, as a blood sample 12 flows through the inlet port 32 and into the flow channel 34, the blood separation device 10 provides passive and fast mixing of the blood sample 12 with the sample stabilizer.

Referring to FIGS. 1-4, in one embodiment, the drive device 13 may comprise an electronic durable component that is in the shape of a standard pipette which drives the flow of blood through the blood separation cartridge 11 and drives the flow of plasma into a point-of-care testing device 22. In one embodiment, the drive device 13 drives flow by vacuum or pressure and can actuate any required valves on the blood separation cartridge 11. The drive device 13 can be battery operated or plugged into a wall outlet in some embodiments or, like some automated pipettes, use induction or plug-in charging with an internal rechargeable battery. In one embodiment, the drive device 13 may include an actuation member 60 and flow in or out is controlled by pressing the actuation member 60 on the top of the drive device 13 in a similar location to a plunger on a standard laboratory pipette. In other embodiment, the actuation member 60 or buttons may be located in a trigger position on the handle similar to automated serological pipettes.

Figure 11:
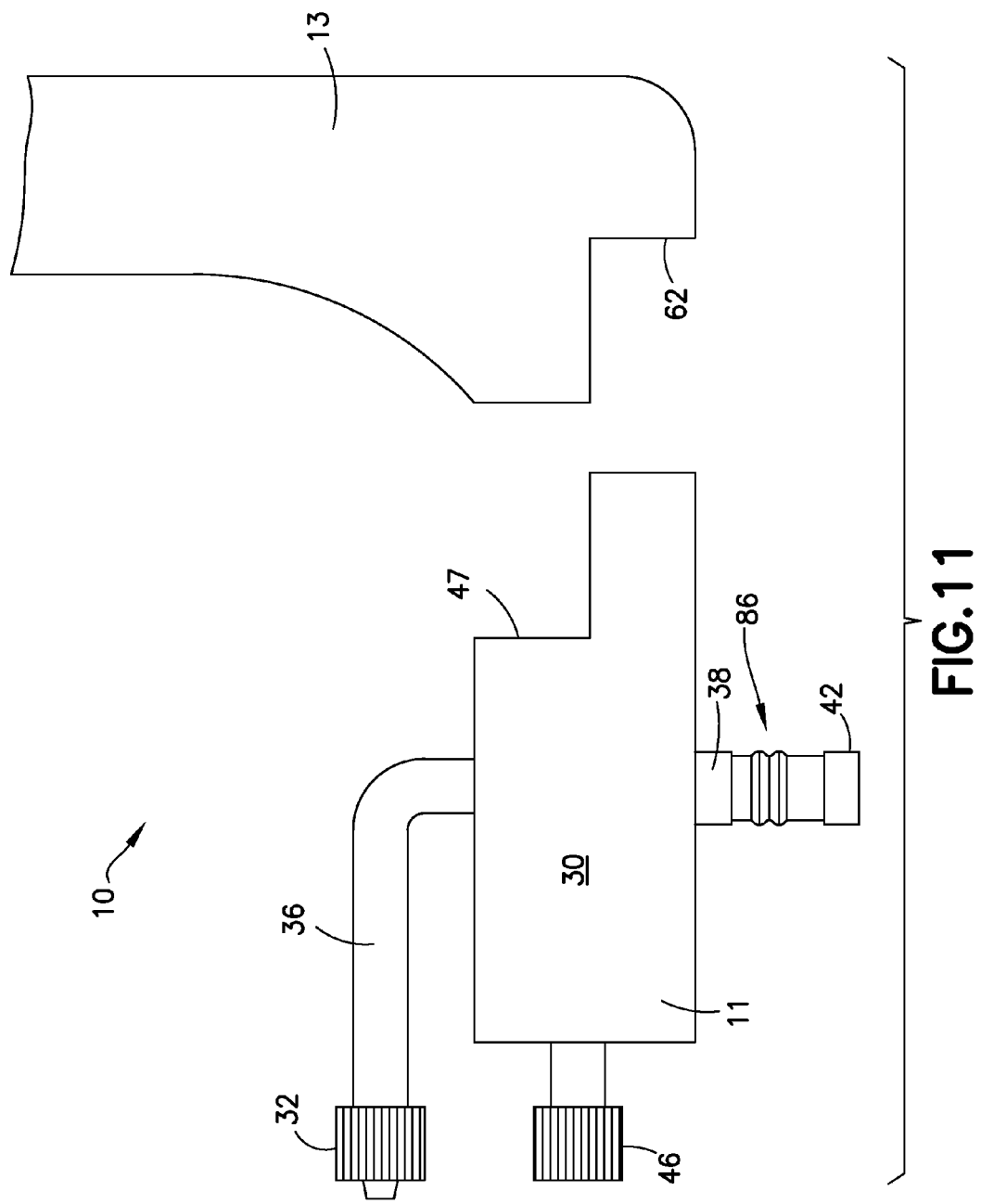
FIG. 11 is a side elevation view of a biological fluid separation device in accordance with an embodiment of the present invention, with a first component being removed from a second component.

The blood separation cartridge 11 and the drive device 13 are removably connectable theretogether such that significant relative movement between the blood separation cartridge 11 and the drive device 13 is prevented. Referring to FIG. 11, in one embodiment, the blood separation cartridge 11 and the drive device 13 are removably connectable theretogether via engagement of a first securement portion 47 of the blood separation cartridge 11 with a second securement portion 62 of the drive device 13. In other embodiments, similar connection mechanisms may be used. For example, a snap fit engagement mechanism or a friction fit engagement mechanism may be used. With the blood separation cartridge 11 and the drive device 13 connected, the blood separation cartridge 11 is adapted to receive a blood sample 12 therein. In one embodiment, the inlet port 32 of the blood separation cartridge 11 is adapted to receive the blood sample upon actuation of the actuation member 60 of the drive device 13 as discussed in more detail below.

Figure 3:
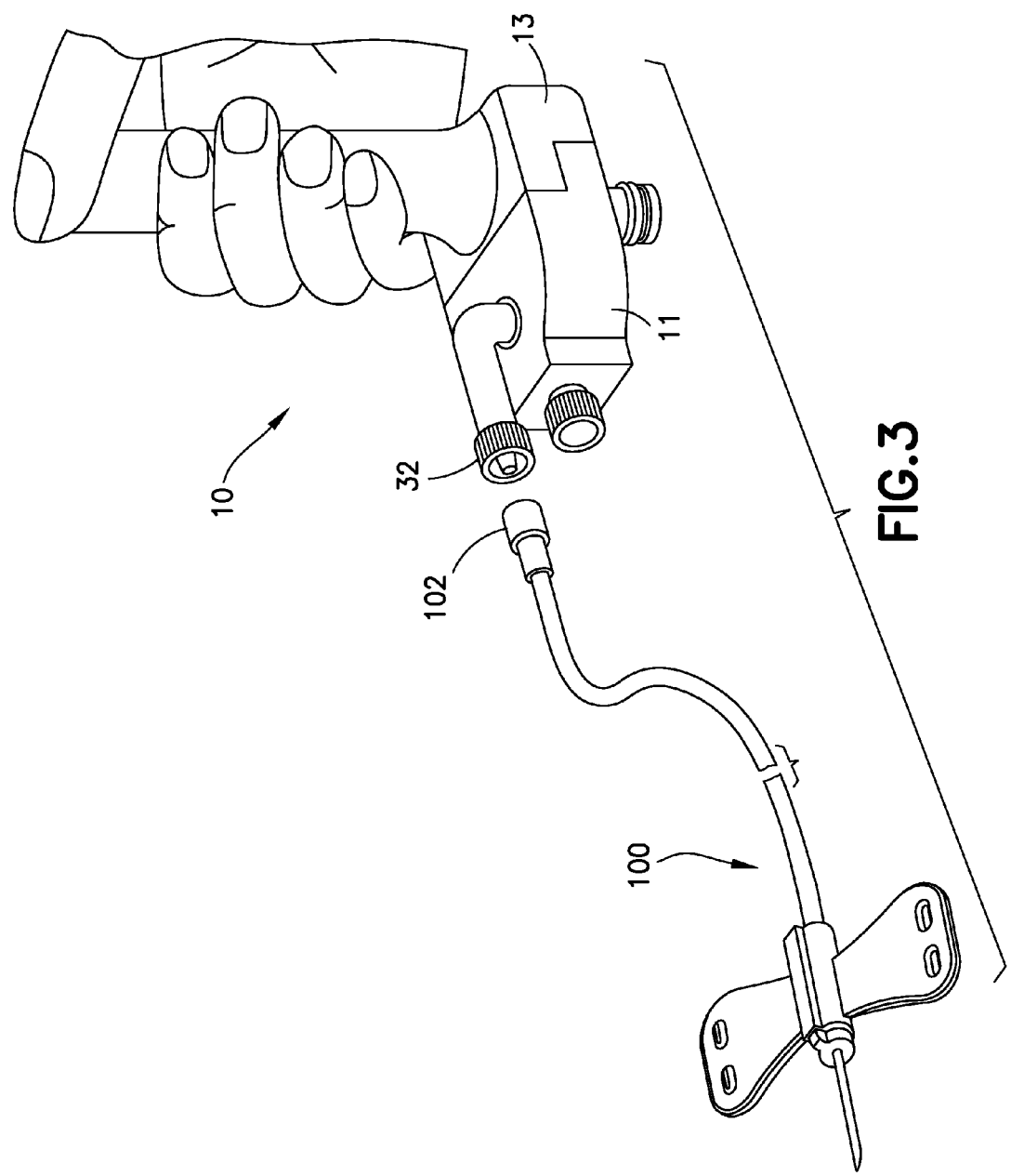
FIG. 3 is a perspective view of a biological fluid separation device in accordance with an embodiment of the present invention, with a first biological fluid collection device.
Figure 4:
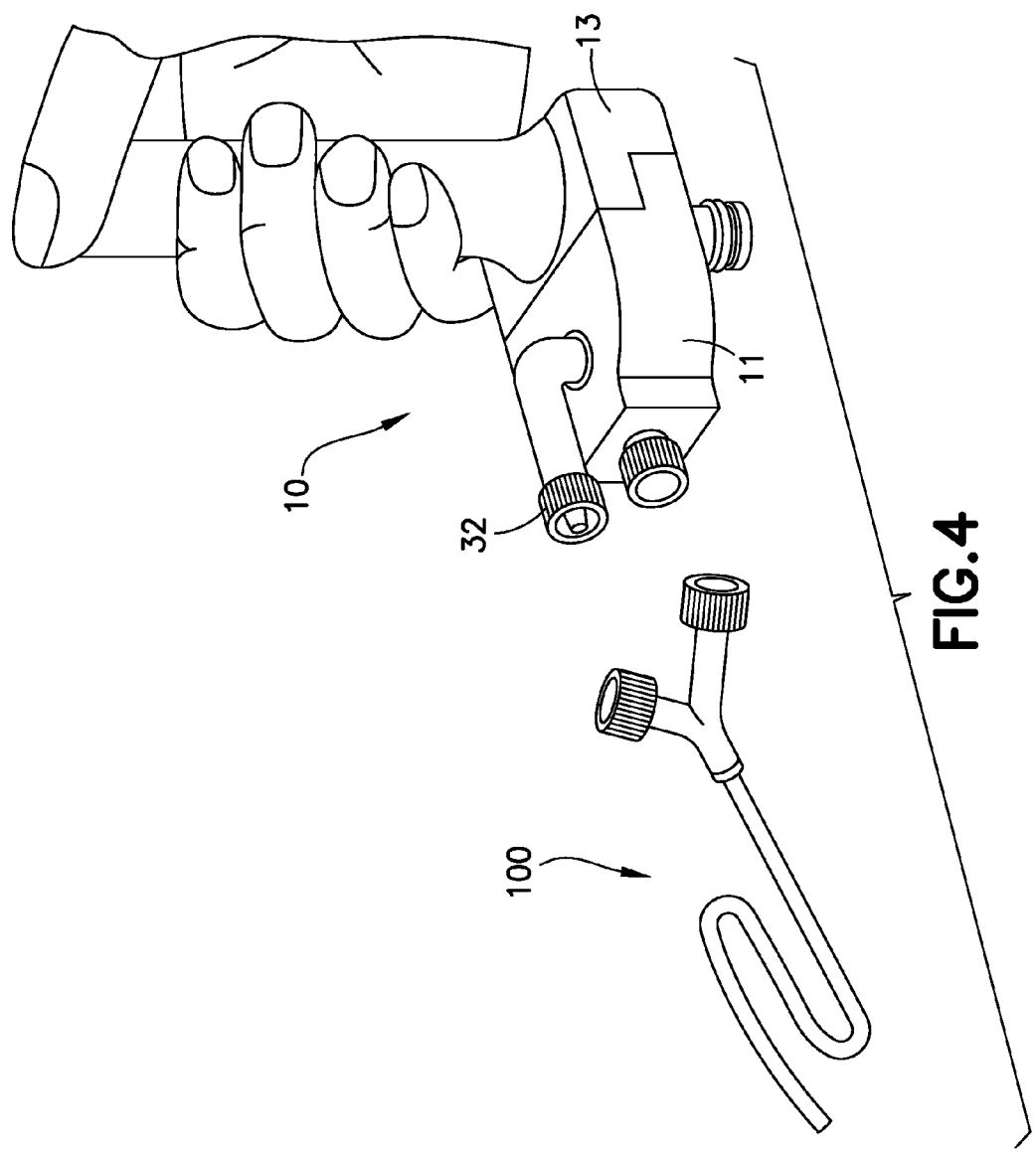
FIG. 4 is a perspective view of a biological fluid separation device in accordance with an embodiment of the present invention, with a second biological fluid collection device.
Figure 5:
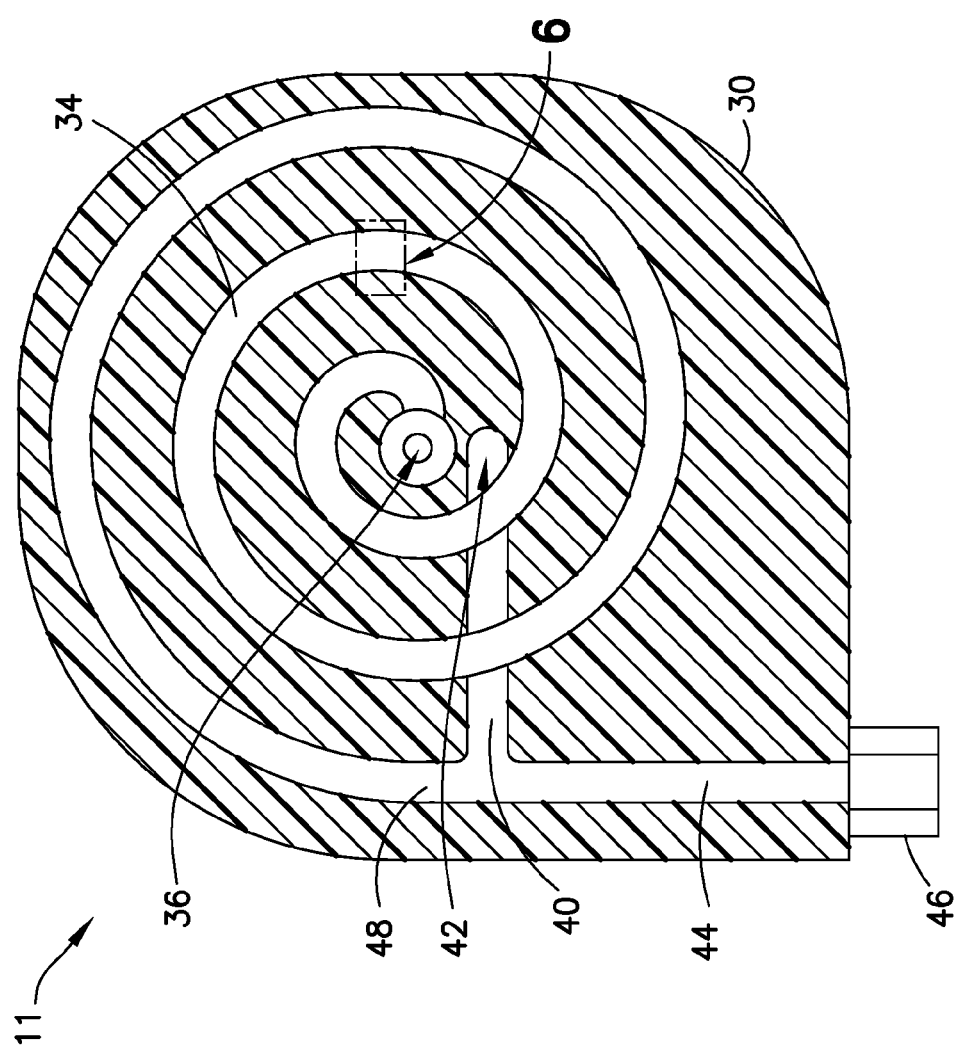
FIG. 5 is a cross-sectional, top view of a biological fluid separation cartridge in accordance with an embodiment of the present invention.

Referring to FIGS. 3 and 4, the inlet port 32 of the blood separation cartridge 11 is adapted to be connected to a blood collection set or blood collection device 100 to allow for the collection of a blood sample 12 into the blood separation device 10. The inlet port 32 may be sized and adapted for engagement with a separate device, such as a needle assembly or IV connection assembly and, therefore, may include a mechanism for such engagement as is conventionally known. For example, in one embodiment, the inlet port 32 may include a luer lock or luer tip for engagement with an optional separate luer mating component of such a separate device for attachment therewith. For example, referring to FIGS. 3 and 4, the blood collection set 100 may include a luer component 102 for engagement with the inlet port 32 of the blood separation device 10. In this manner, the inlet port 32 is connectable to the blood collection set 100 for the collection of a blood sample into the blood separation device 10. In addition, a mechanism for locking engagement between the inlet port 32 and the blood collection set 100 may also be provided. Such luer connections and luer locking mechanisms are well known in the art. The blood collection set 100 may include a needle assembly, an IV connection assembly, a PICC line, an arterial indwelling line, or similar blood collection means.

The inlet port 32 may also include a resealable septum that is transitionable between a closed position and an open position. With the septum in an open position, a blood sample 12 may flow through the inlet port 32 to the flow channel 34 via the inlet channel 36.

The blood separation cartridge 11 also may include a valve or septum 86 (FIGS. 8 and 9) at the first outlet port 42. The first outlet port 42 is adapted for connection to a point-of-care testing device 22 for closed transfer of a portion of the plasma portion 16 from the blood separation device 10 to the point-of-care testing device 22 via the first outlet port 42 as described in more detail below. The valve or septum 86 at the first outlet port 42 is transitionable between a closed position and an open position. With the valve or septum 86 in an open position (FIG. 9), the plasma portion 16 of the blood sample 12 may flow through the first outlet port 42 to a blood testing device or a point-of-care testing device 22 (FIG. 7).

Referring to FIG. 7, a blood testing device or point-of-care testing device 22 includes a receiving port 24 adapted to receive the first outlet port 42 of the blood separation device 10. The blood testing device 22 is adapted to receive the first outlet port 42 of the blood separation device 10 for closed transfer of a portion of the plasma portion 16 (FIG. 6) from the blood separation device 10 to the blood testing device 22. The blood testing device 22 is adapted to receive the plasma portion 16 to analyze the blood sample and obtain test results.

As discussed above, the first outlet port 42 of the blood separation device 10 may include a valve or septum 86 that is transitionable between a closed position and an open position. With the valve or septum 86 in an open position (FIG. 9), the plasma portion 16 of the blood sample 12 may flow through the first outlet port 42 to a blood testing device or a point-of-care testing device 22 (FIG. 7).

Figure 9:
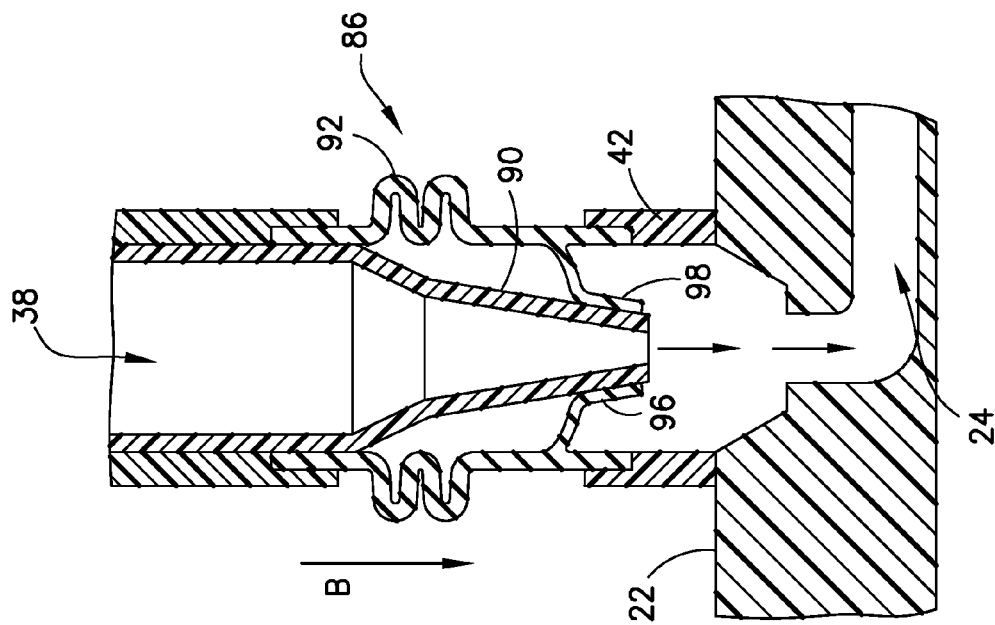
FIG. 9 is a cross-sectional view of a septum of a biological fluid separation device in accordance with an embodiment of the present invention, with the septum in an open position.
Figure 8:
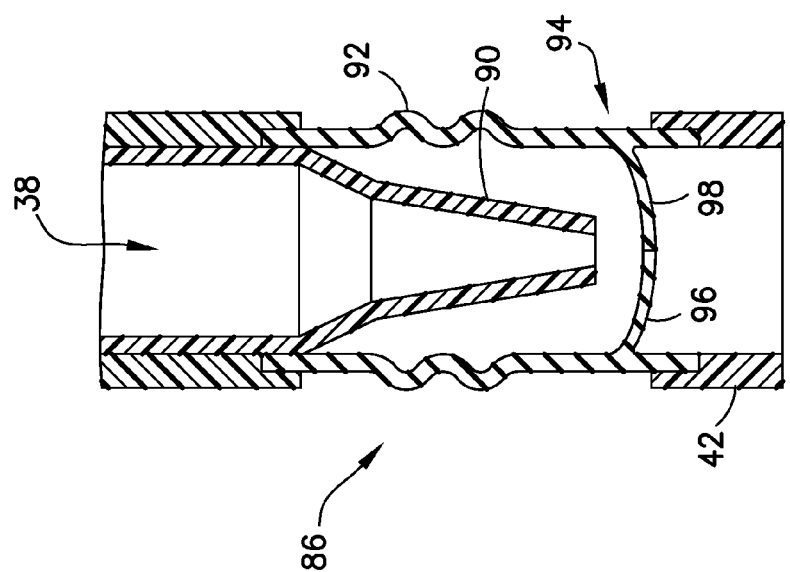
FIG. 8 is a cross-sectional view of a septum of a biological fluid separation device in accordance with an embodiment of the present invention, with the septum in a closed position.

In one embodiment, referring to FIGS. 8 and 9, the valve 86 may generally include a transfer channel 90, a bellows or deformable wall member 92, and a septum or barrier 94 having a first barrier wall 96 and a second barrier wall 98. Referring to FIG. 8, the valve 86 is in a closed position to prevent the plasma portion 16 of the blood sample 12 from flowing through the first outlet port 42. In this manner, the plasma portion 16 is sealed within the blood separation device 10. Referring to FIG. 9, the valve 86 is in an open position so that the plasma portion 16 of the blood sample 12 may flow through the first outlet port 42 to a blood testing device or a point-of-care testing device 22 (FIG. 7).

Referring to FIG. 9, with the plasma portion 16 received within the first outlet port 42 of the blood separation device 10, the first outlet port 42 of the blood separation device 10 is then positioned over the receiving port 24 of the point-of-care testing device 22. Pushing down in the direction of arrow B compresses the deformable wall member 92 and opens up the first barrier wall 96 and the second barrier wall 98 of the septum 94 as shown in FIG. 9. With the valve 86 in the open position, the plasma portion 16 of the blood sample 12 is allowed to flow through the first outlet port 42 and the receiving port 24 to the point-of-care testing device 22 in a closed manner, reducing exposure to the clinician and the patient.

The valve 86 of the blood separation device 10 only opens when the first outlet port 42 is pressed upon the receiving port 24 of the point-of-care testing device 22. This releases the isolated plasma portion 16 directly into the receiving port 24 of the point-of-care testing device 22, thus mitigating unnecessary exposure to the patient's blood.

Referring to FIGS. 10 and 11, a blood separation system of the present disclosure will now be discussed. In one embodiment, the drive device 13 is connectable with any number of blood separation cartridges 11. In this manner, a blood separation cartridge 11 is a replaceable single use component. As will be described below, after use of a blood separation cartridge 11, the blood separation cartridge 11 can be removed from the drive device 13, as shown in FIG. 11, and the blood separation cartridge 11 can be disposed of into a biological hazard container. When it is desired to use the blood separation device 10 again, a new and clean blood separation cartridge 11 can be selected and used with the drive device 13. One advantage of the blood separation system of the present disclosure is that a plurality of blood separation cartridges 11 can be used with the drive device 13. The drive device 13 can be repeatedly used.

Referring to FIGS. 1-11, use of a blood separation device and blood separation and testing system of the present disclosure will now be described. Referring to FIGS. 3 and 4, the inlet port 32 of the blood separation device 10 is adapted to be connected to a blood collection set 100 to allow for the collection of a blood sample 12 into the blood separation device 10 as discussed above. Once the blood collection set 100 is connected to a patient, the actuation member 60 of the drive device 13 is activated, e.g., a power switch is pushed down, to draw the blood sample into the flow channel 34 of the blood separation cartridge 11. As the blood sample 12 slowly fills the blood separation device 10, it is collected and stabilized over a layer of sample stabilizer. Referring to FIG. 6, the blood sample 12 may then flow through the flow channel 34 for inertial separation of the cellular portion 14 from the plasma portion 16. Inside of the flow channel 34, the series of posts 52 are arranged to enhance plasma separation by filtering and directing the cellular portion 14 to the outside of the flow channel 34, which is the same direction that the inertial forces drive the cellular portion 14.

At the end of the flow channel 34, e.g., the junction point 48, the flow channel 34 splits into a first collection chamber 40 for collecting the plasma portion 16 and a second collection chamber 44 for collecting the cellular portion 14. The first collection chamber 40 and the second collection chamber 44 include no posts 52 to take advantage of laminar flow properties in a microfluidic channel. In one embodiment, to increase throughput, multiple spirals can be fabricated that operate in parallel to generate sufficient plasma volume for a downstream application. The first collection chamber 40 includes the first outlet port 42 which interfaces with a point-of-care testing device 22 or storage vessel.

After disconnecting the blood separation device 10 from the blood collection set 100 or other blood collection line, the blood separation device 10 may be engaged with a blood testing device 22. Next, the first outlet port 42 is placed over the receiving port 24 of the point-of-care testing device 22 as shown in FIG. 7. Then, the actuation member 60 of the drive device 13 may be activated or depressed to advance the plasma portion 16 and to transfer the collected plasma portion 16 to the point-of-care testing device 22. The blood testing device 22 is adapted to receive the first outlet port 42 of the blood separation device 10 for closed transfer of a portion of the plasma portion 16 from the blood separation device 10 to the blood testing device 22. The blood testing device 22 is adapted to receive the plasma portion 16 to analyze the blood sample and obtain test results. After that, the blood separation cartridge 11 can be removed from the drive device 13, as shown in FIG. 11, and the blood separation cartridge 11 can be disposed of into a biological hazard container.

Current systems for blood collection use centrifugation of blood collection tubes often in a centralized lab to generate plasma. This limits the ability to use plasma for point-of-care testing. The blood separation system of the present disclosure relies on inertial forces and a gentler filtration to generate plasma. The filtration posts are made of the same material as the device so analyte bias and passivation is the same for the posts as the parent device. By using the two methods to drive the cellular portion into a separate flow stream, less filtration should be required to generate the same quality plasma.

Some of the other advantages of the blood separation device and the blood separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to the point-of-care testing device 22. The blood separation device of the present disclosure enables integrated blood collection and plasma creation in a closed system without centrifugation. The clinician may collect and separate the blood sample and then immediately transfer the plasma portion to the point-of-care testing device 22 without further manipulation. This enables collection and transfer of plasma to the point-of-care testing device 22 without exposure to blood. In addition, the blood separation device of the present disclosure minimizes process time by processing the blood within the blood separation device and without external machinery. Further, for tests which only require small amounts of blood, it eliminates the waste associated with blood collection and plasma separation with an evacuated tube.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid separation cartridge, comprising:
    a housing having a single inlet port and a flow channel defined within the housing in fluid communication with the single inlet port, the flow channel having a spiral shape;
    a first collection chamber defined within the housing in fluid communication with the flow channel and including a first outlet port having a valve;
    a second collection chamber defined within the housing in fluid communication with the flow channel and including a second outlet port, the second collection chamber isolated from the first collection chamber, and the second outlet port spaced apart from the first outlet port; and
    an inlet channel in fluid communication with the single inlet port and the flow channel, wherein at least one of the inlet channel and the flow channel contains a sample stabilizer therein,
    wherein the valve comprises a deformable wall member and a septum, and wherein the septum covers the first outlet port.

2. The biological fluid separation cartridge of claim 1, wherein the biological fluid separation cartridge receives a multi-component blood sample.

3. The biological fluid separation cartridge of claim 2, wherein the multi-component blood sample comprises a cellular portion and a plasma portion.

4. The biological fluid separation cartridge of claim 3, wherein the flow channel comprises a separation element that separates the cellular portion and the plasma portion of the multi-component blood sample.

5. The biological fluid separation cartridge of claim 4, wherein the separation element comprises a plurality of posts.

6. The biological fluid separation cartridge of claim 2, wherein the single inlet port includes a connecting portion that engages a blood collection device and the single inlet port receives the multi-component blood sample via connection to the blood collection device.

7. The biological fluid separation cartridge of claim 3, wherein the first collection chamber receives at least a portion of the plasma portion therein and the second collection chamber receives at least a portion of the cellular portion.

8. The biological fluid separation cartridge of claim 7, further comprising a one-way mechanism for preventing the cellular portion from entering the first collection chamber.

9. The biological fluid separation cartridge of claim 3, wherein the first outlet port is adapted for connection to a point-of-care testing device for closed transfer of a portion of the plasma portion from the first collection chamber to the point-of-care testing device.

10. The biological fluid separation cartridge of claim 9, further comprising a connection portion that engages a drive device, wherein with the drive device connected to the biological fluid separation cartridge, the drive device causes flow of the plasma portion from the first collection chamber to the point-of-care testing device.

11. A biological fluid separation and testing system for a multi-component blood sample, the biological fluid separation and testing system comprising:
    a biological fluid separation cartridge adapted to receive the multi-component blood sample, the biological fluid separation cartridge comprising:
        a housing having a single inlet port and a flow channel defined within the housing in fluid communication with the single inlet port, the flow channel have a spiral shape;
        a first collection chamber defined within the housing in fluid communication with the flow channel and including a first outlet port having a valve;
        a second collection chamber defined within the housing in fluid communication with the flow channel and including a second outlet port, the second collection chamber isolated from the first collection chamber, and the second outlet port spaced apart from the first outlet port; and
        an inlet channel in fluid communication with the single inlet port and the flow channel, wherein at least one of the inlet channel and the flow channel contains a sample stabilizer therein,
        wherein the valve comprises a deformable wall member and a septum, and wherein the septum covers the first outlet port; and
    a blood testing device having a receiving port adapted to receive the first outlet port of the biological fluid separation cartridge for closed transfer of a portion of a component of the multi-component blood sample from the first collection chamber to the blood testing device.

12. The biological fluid separation and testing system of claim 11, wherein the multi-component blood sample comprises a first cellular portion component and a second plasma portion component.

13. The biological fluid separation and testing system of claim 12, further comprising a connection portion that engages a drive device, wherein with the drive device connected to the biological fluid separation cartridge, the drive device causes flow of the plasma portion from the first collection chamber to the blood testing device.

14. The biological fluid separation and testing system of claim 11, wherein the blood testing device comprises a point-of-care testing device.

* * * * *